United States Patent [19]

Nambu

[11] Patent Number: 4,895,157

[45] Date of Patent: Jan. 23, 1990

[54] MAGNETIC RESONANCE IMAGING SYSTEM

[75] Inventor: Kyojiro Nambu, Tochigi, Japan

[73] Assignee: Kabushiki Kaisha Toshiba, Kawasaki, Japan

[21] Appl. No.: 155,572

[22] Filed: Feb. 12, 1988

[30] Foreign Application Priority Data

Feb. 16, 1987 [JP] Japan ................................ 62-32874

[51] Int. Cl.[4] .............................................. A61B 5/04
[52] U.S. Cl. ................................ 128/653 A; 128/696; 324/309
[58] Field of Search ............... 128/696, 698, 701, 716, 128/721, 653; 324/309

[56] References Cited

U.S. PATENT DOCUMENTS

| | | | |
|---|---|---|---|
| 4,564,017 | 1/1986 | Glover | 128/721 X |
| 4,694,836 | 9/1987 | Builkman et al. | 128/653 |
| 4,694,837 | 9/1987 | Blakely et al. | 128/696 X |
| 4,712,560 | 12/1987 | Schaefer et al. | 128/721 X |
| 4,718,424 | 1/1988 | Nishimura | 128/653 |
| 4,724,386 | 2/1988 | Hasche et al. | 128/721 X |
| 4,727,882 | 3/1988 | Schneider et al. | 128/721 X |
| 4,730,620 | 3/1988 | Bailes | 128/721 X |
| 4,739,766 | 4/1988 | Riederer | 128/653 |

FOREIGN PATENT DOCUMENTS

3421045A1 12/1985 European Pat. Off. .
3514542AL 10/1986 European Pat. Off. .

Primary Examiner—Francis Jaworski
Attorney, Agent, or Firm—Foley & Lardner, Schwartz, Jeffery, Schwaab, Mack, Blumenthal & Evans

[57] ABSTRACT

A magnetic resonance imaging system applies repeatedly gradient magnetic fields and a high frequency magnetic field in a predetermined sequence according to an phase encoding method to a region including a selected slice of a subject having a varying portion which periodically varies and in which substantially at least two conditions alternately appear, in order to excite a magnetic resonance phenomenon in the selected slice, acquire a magnetic resonance signal due to the magnetic resonance phenomenon, and obtain magnetic resonance imaging information of the selected slice from the acquired magnetic resonance signal. The system comprises a variation detector for monitoring the variation of the varying portion of the subject, and detecting timings corresponding to the two conditions. The system is responsive to the variation detector to control the repetition of the predetermined sequence and acquire alternately magnetic resonance signals in the two conditions.

5 Claims, 9 Drawing Sheets

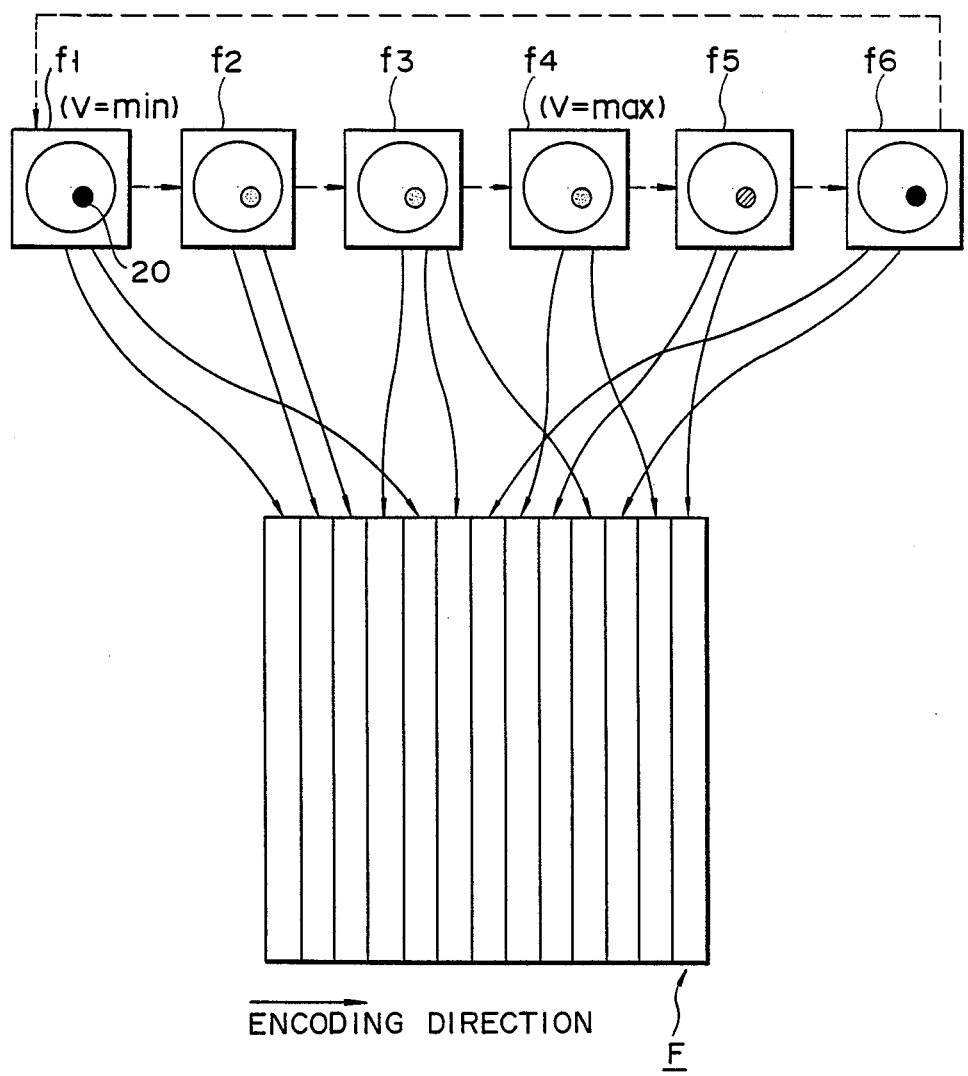
F I G. 4

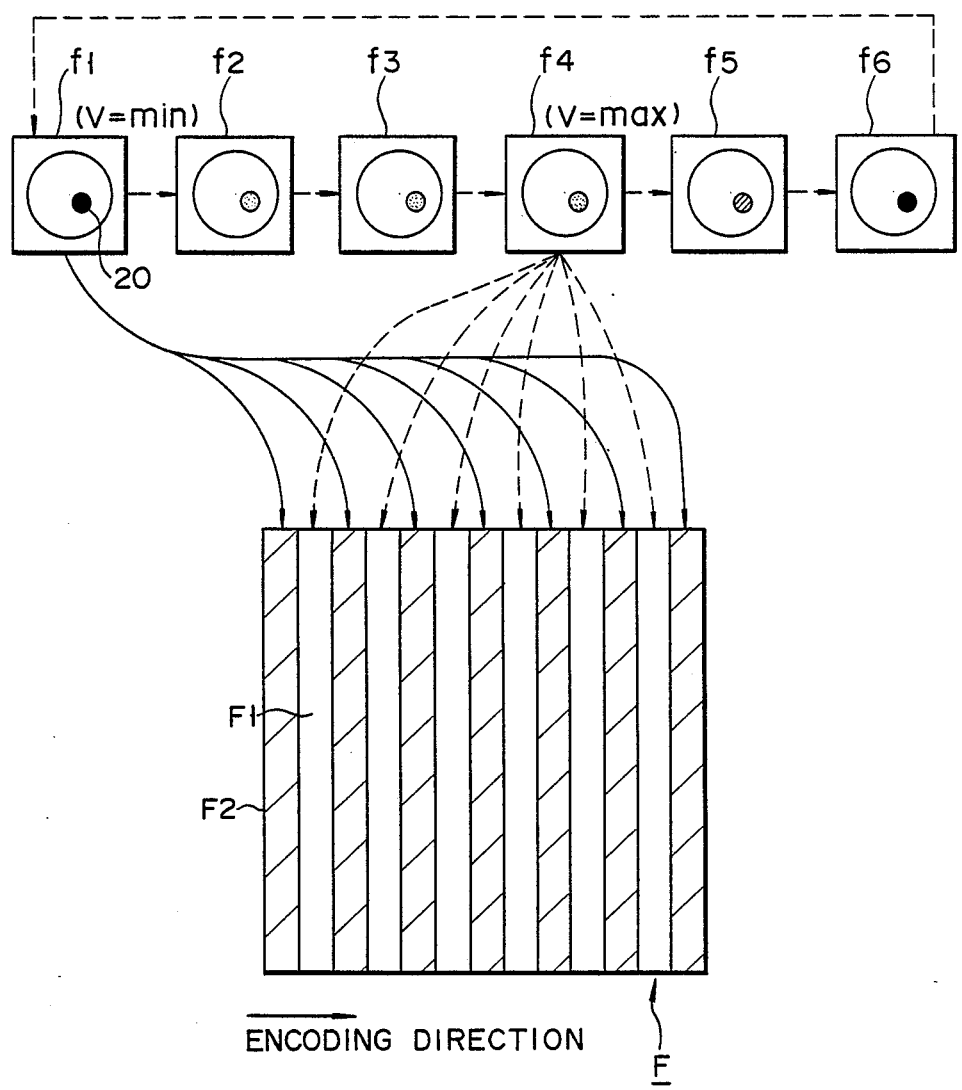
F I G. 8

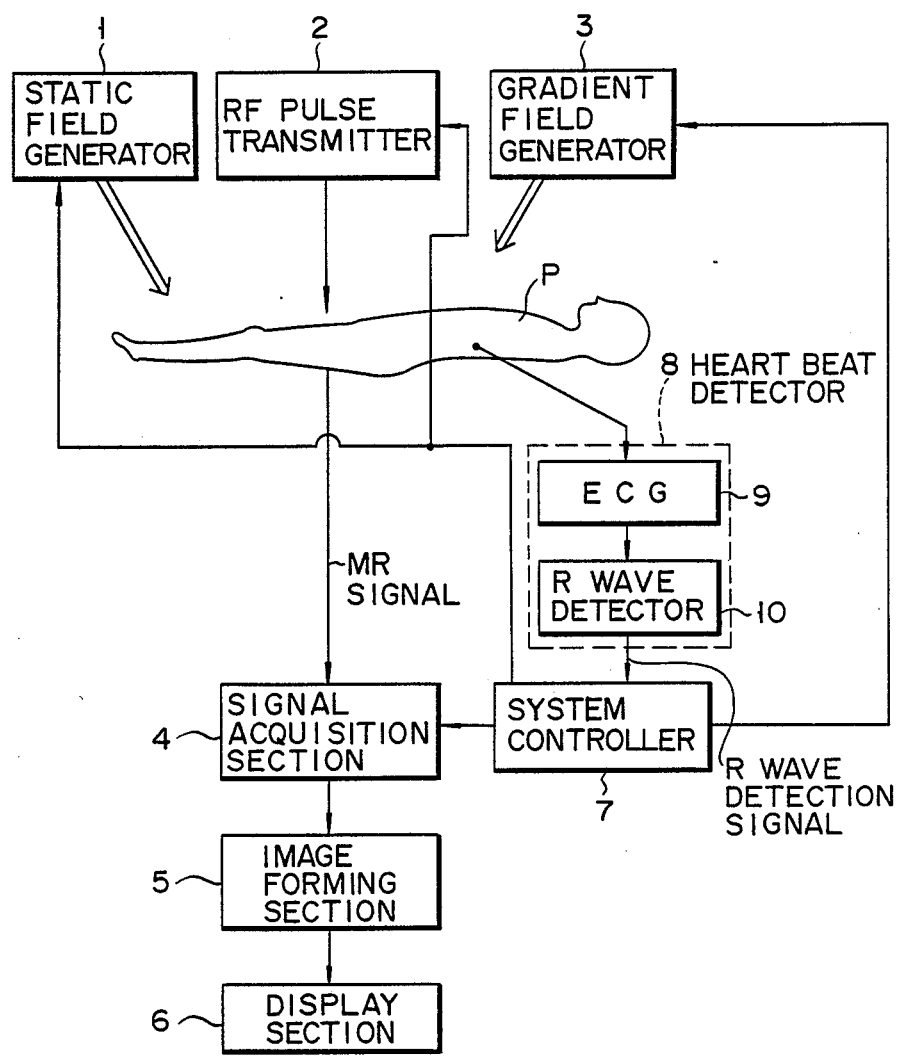
F I G. 18

MAGNETIC RESONANCE IMAGING SYSTEM

BACKGROUND OF THE INVENTION

1. Field of the Invention:

This invention relates to a magnetic resonance imaging (MRI) system for obtaining magnetic resonance (MR) images of a selected slice of an object which may involve, a living subject. More specifically, this invention relates to an MRI system capable of reducing the degradation in the MR images which is caused by image artifacts or false images resulting from variations in MR information obtained from regions of the object, such as blood vessels whose MR information periodically varies due to the varying flow rate of blood.

b 2. Description of the related art including information disclosed under §§1.97-1.99

In MRI systems, a subject (patient) on an examination table or couch is placed in a static homogeneous magnetic field, and a high frequency magnetic field, usually RF (radio frequency) magnetic field is applied to the subject in a direction orthogonal to the static magnetic field. As a result, a magnetic resonance phenomenon is induced in nuclear spins in the subject. After the removal of the RF magnetic field, a magnetic resonance (MR) signal generated by the resonated nuclear spins is detected and collected to form an MR image. For the excitation of the magnetic resonance and the collection of the MR signal, in general, some gradient magnetic fields are applied to a predetermined portion of the subject.

As one of typical imaging methods for the MRI systems the two-dimensional Fourier transform (2DFT) method is well known, which uses a technique called phase encoding method in order to obtain two-dimensional position information in a selected slice of a subject.

Where this phase encoding method is used, a pulsed RF magnetic field, i.e. an RF pulse, and plural pulsed gradient magnetic fields are used. The gradient magnetic fields involve a slicing gradient magnetic field adapted for selecting a slice of the subject to obtain an MR image, and also a phase encoding gradient magnetic field and a readout gradient magnetic field, both adapted for adding two-dimensional position information to a detected MR signal.

Reference is now made to FIGS. 1A through 1E to describe a pulse sequence of the RF pulse and gradient magnetic fields in the phase encoding method.

A 90° RF pulse and a 180° RF pulse in FIG. 1A, a slicing gradient magnetic field Gz in FIG. 1B, a phase encoding gradient magnetic field Gy in FIG. 1C, and a readout gradient magnetic field Gx in FIG. 1D are generated during a repetition time TR at respective timings shown in FIGS. 1A through 1D. This pulse sequence is repeated. The encoding gradient magnetic field Gy has its intensity (the magnitude of gradient) changed by a predetermined amount each time the pulse sequence is repeated. In this way, the MR signal can be gathered which include two-dimensional position information about the selected slice of the subject. The MR signal include an FID (free induction decay) signal and a spin-echo signal. However, the widely used spin-echo method detects and collects the spin-echo signal only.

The collected MR signal is then subjected to the two-dimensional Fourier transform, i.e. Fourier transforms in the x and y directions to form or reconstruct an MR image for the selected slice of the subject.

According to the existing systems, however, where a slice of the subject to be examined, or a reconstructed MR image thereof includes such an MR-information varying portion as an image of an aorta whose MR information varies owing to varying flow rate of blood, image artifacts would appear in the finally obtained MR image which are due to the variation in the MR information. This adversely affects the diagnosis of the subject under examination based on the MR image.

To collect the MR information within a sufficiently short time as compared to the rate of MR-information variation may prevent the image artifacts from being generated. It is impossible, however, to collect enough MR signals to reconstruct an MR image within such a short time. An existing system uses a technique for collecting an MR signal within a very short time, in synchronism with a cycle of variation of an MR-information varying portion and in a specified phase condition of the MR-information variation, in which case, however, it requires a long period of time to collect enough MR signals to reconstruct an MR image.

SUMMARY OF THE INVENTION

It is an object of this invention to provide an MRI system capable of effectively reducing MR image degradation resulting from image artifacts due to a varying portion in a selected slice of subject under examination, and obtaining a substantially effective MR image, so long as the varying portion in the slice of the subject to be examined periodically varies and has substantially at least two conditions which appear alternately.

An MRI system of this invention applies predetermined gradient magnetic fields and high-frequency magnetic field, in a predetermined sequence according to phase encoding method, to a region of a subject including a selected slice having a varying portion which periodically varies and in which substantially at least two conditions appear alternately, in order to excite a magnetic resonance signal in the selected slice of the subject and to collect the magnetic resonance signal due to the magnetic resonance phenomenon. The magnetic resonance imaging information for the selected slice is obtained from the collected magnetic resonance signal. The system is provided with a variation detector which monitors the variation of the varying portion of the subject and detects timings of the appearance of the above two conditions. The system responds to the variation detector to control the repetition of the predetermined pulse sequence, and alternately collect magnetic resonance signals in the above two conditions.

According to the MRI system of this invention, so long as the varying portion varies periodically and has substantially at least two conditions that appear alternately, the MR signals can be collected in a short time, and the image artifacts can be located at positions sufficiently remote from the varying portion so that an MR image is obtained that has reduced the adverse effect due to the image artifacts.

BRIEF DESCRIPTION OF THE DRAWINGS

FIGS. 2 through 17 are diagrams used for explaining the principle of an embodiment of this invention, more specifically, FIGS. 2 through 6 are used for explaining the generation of image artifacts due to blood flow, and FIGS. 7 through 17 are used for explaining the excitation of magnetic resonance, the collection of MR signals, and the resultant MR image according to the embodiment of this invention; and FIG. 18 is a block diagram of an MRI system embodying this invention.

DETAILED DESCRIPTION OF THE PREFERRED EMBODIMENT

First, the principle of an MRI system of this invention will be described.

The generation of image artifacts resulting from a varying portion such as the aorta of a human body which causes a variation in MR information therefor because of blood flow will be discussed.

Figure 2:
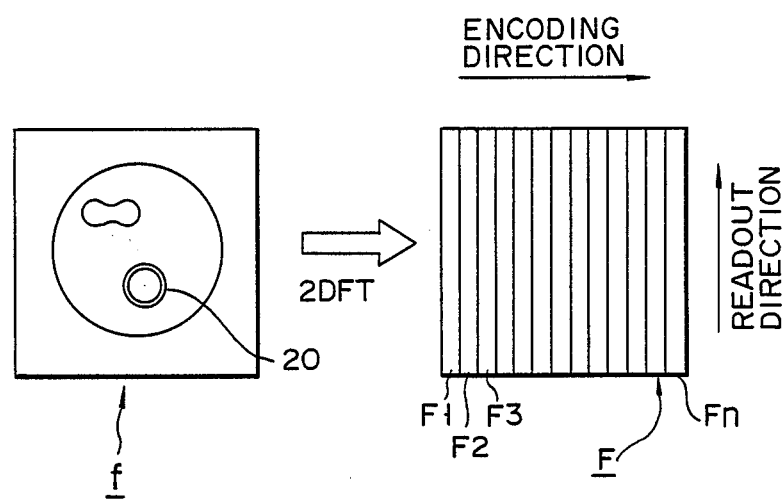

In FIG. 2, the letter f stands for the image of a selected slice of a subject, and the letter F a two-dimensional Fourier transformed image of f. According to the phase encoding method data groups for columns designated F1, F2, F3, ..., Fn (n is an integer) are sequentially acquired for each repetition of the pulse sequence. Each of columns F1 ~ Fn extends in the readout direction of sampling lattice points on the two-dimensional Fourier transformed (2DFT) image F, and columns F1 ~ Fn are arranged in the encoding direction, or the direction of the phase encoding magnetic field gradient, the number of which being equal to the frequency of encoding operations (the number of times of the pulse sequence repetition.)

Figure 3A:
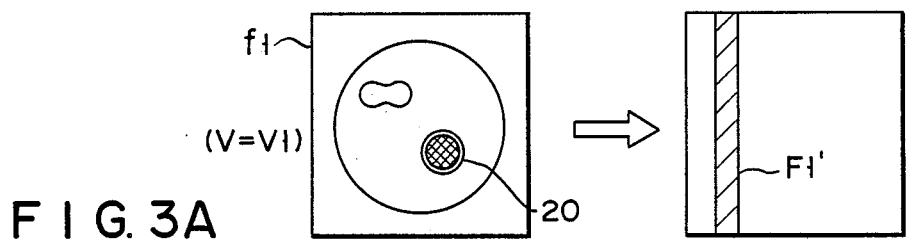
Figure 3B:
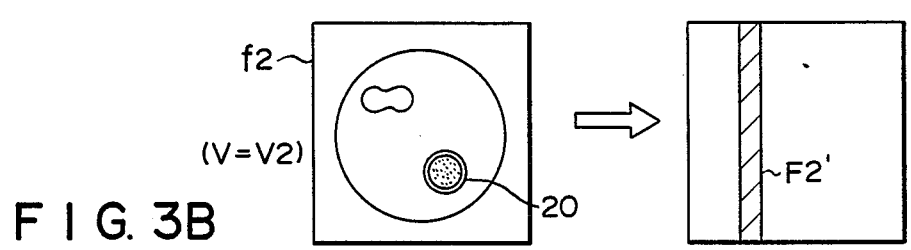
Figure 3C:
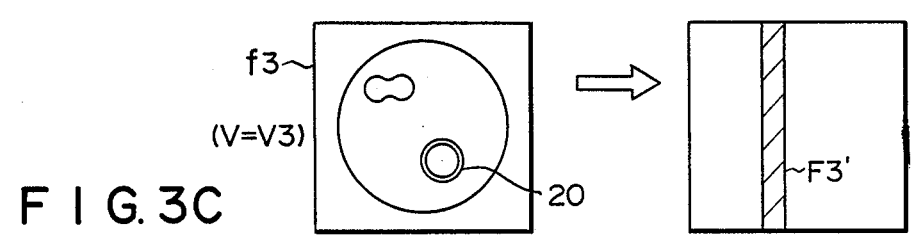

However, where aorta 20, which is a varying portion in slice image f, varies with variations of blood flow rate during data acquisition, as shown in FIGS. 3A to 3C, columns F1', F2', and F3' in 2DFT image F correspondingly respectively to slice images f1, f2, and f3 for different values v1, v2, and v3 of time-varying blood flow rate v will be arranged at random, thus forming 2DFT image F. Different blood flow rates will usually produce different image density or gradations on MR image, and often vary the shape or the size of blood vessel.

Figure 5:
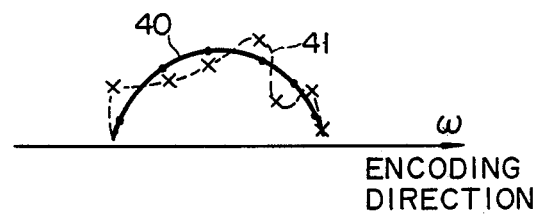
Figure 6:
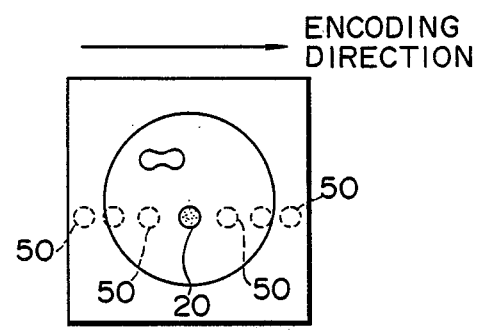

More specifically, since the variation of blood flow rate dependent on heartbeats and the repetition operation of the sequence of MR signal acquisition are not synchronized with each other, images f1 ~ f6 corresponding to different values of periodically varying blood flow rate v are extracted in the form of columns of 2DFT image F, and then arranged at random as shown in FIG. 4. Thus, as shown in FIG. 5, a profile of 2DFT data in the encoding direction will abruptly vary as shown at 41, compared with an optimum profile 40 in the case where no varying portion is involved. As a result, as shown in FIG. 6, many image artifacts 50 will appear in the encoding direction from the center to opposite ends of a reconstructed MR image for obtained by two-dimensional discrete inverse Fourier transforming the 2DFT image F in the MRI system.

Figure 7:
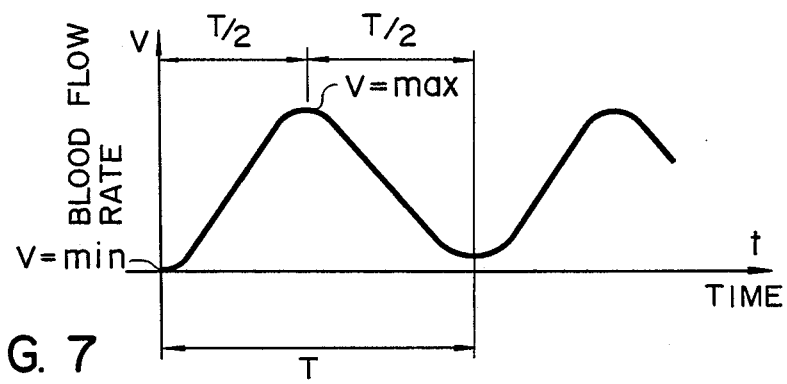

For this reason, according to this invention, the pulse sequence is controlled to repeat in synchronism with heartbeats of the subject and at an interval of approximately half the period of the heartbeats. More specifically, where the period of the heartbeats is T as shown in FIG. 7, the excitation of the MR phenomenon and the collection of the MR signal according to the phase encoding method are carried out repeatedly at an o interval of approximately T/2. Therefore, in the worst case, the blood flow rate v has a minimum value when the excitation of the MR phenomenon and the collection of the MR signal is performed, and a maximum value when the excitation of the MR phenomenon and the collection of the MR signal is performed again. As a result, as shown in FIG. 8, two-dimensional Fourier transformed images F2 and F1 will be alternately obtained from the slice images f1 and f4 corresponding to v = min. and v = max., respectively.

When the variation is continuously periodic like blood flow rate, and it is supposed that $a+b=1$ ($1>a>0$, $1>b>0$), the repetition interval of the pulse sequence for exciting the MR phenomenon and collecting the MR signal should be set to aT, bT, aT, bT, ...

Figure 9:
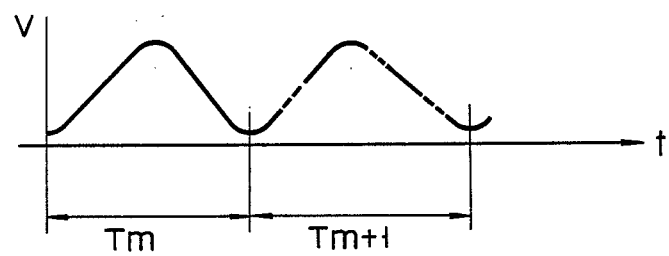

In order to excite the MR phenomenon and collect the MR signals at the above mentioned timings, for example, the heartbeats of the subject are monitored by electrocardiogram (ECG) signals to hold the repetition interval aT, bT of the pulse sequence. The heartbeat period T often varies periodically, in which case, as shown in FIG. 9, the next heartbeat period $Tm+1$ is predicted from the previously observed heartbeat periods $T1 \sim Tm$ so as to excite the MR phenomenon and collect the MR signals at an interval of $aTm+1$ or $bTm+1$.

Figure 10:
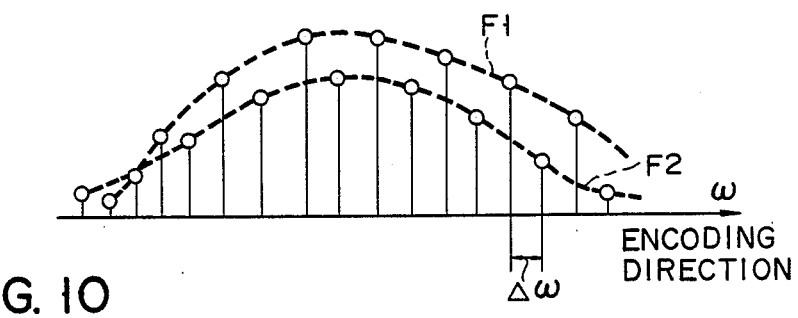
Figure 11:
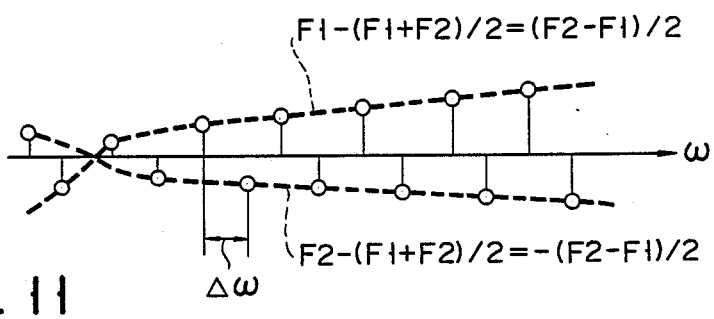

The profile of the 2DFT image F of FIG. 8 in the encoding direction is shown in FIG. 10. In FIG. 10, F1 shows the case where the blood flow rate v is maximum, whereas F2 shows the case where the blood flow rate v is minimum. Referring to FIG. 11, the difference D between F and the average of F1 and F2, i.e. $D = F - \{(F1+F2)/2\}$ is $$F1 - \{(F1+F2)/2\} = -(F2-F1)/2 \quad (1)$$

$$F2 - \{(F1+F2)/2\} = +(F2-F1)/2 \quad (2)$$

As shown in FIG. 11, these equations indicate the reversal of sign of $(F2-F1)/2$ at the encode sampling interval $\Delta\omega$. $D(\omega)$ is represented by $$D(\omega) = \frac{1}{2} \{F2(\omega) - F1(\omega)\} \exp\left(i\frac{\omega\pi}{\Delta\omega}\right) \quad (3)$$

D is a function related to the encoding direction $\omega$ and the readout direction $\psi$. Thus, D should inherently be expressed by $D(\omega, \psi)$, not by $D(\omega)$. However, here, D is represented by $D(\omega)$ for convenience because components related to the readout direction $\psi$ are not involved. The same holds true of $F1(\omega)$ and $F2(\omega)$.

Accordingly, the two-dimensional discrete inverse Fourier transformed image $d(x,y)$ is given by $$d(x,y) = g(x+\pi, y) \quad (4)$$

Figure 12:
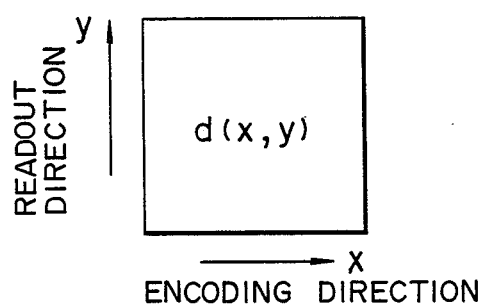

Refer to FIG. 12. It is noted that $g(x,y)$ is given by $$g(x,y) = \frac{f2(x,y) - f1(x,y)}{2} \quad (5)$$

Figure 13:
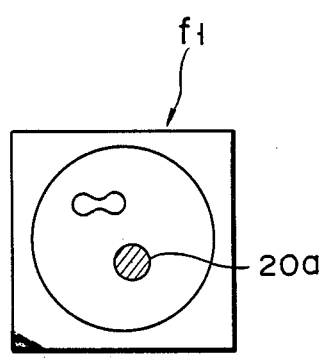
Figure 14:
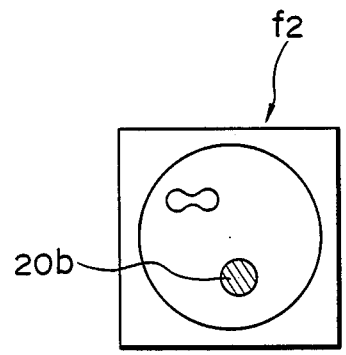
Figure 15:
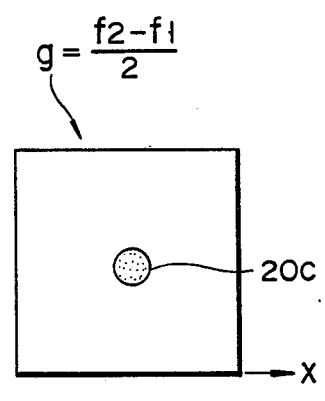
Figure 16:
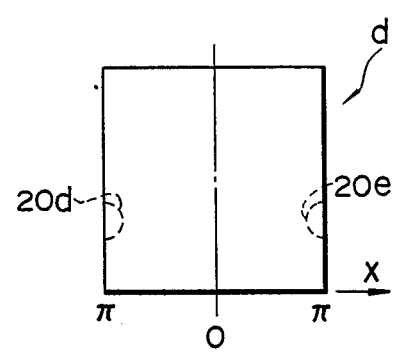

It should be noted that the two-dimensional Fourier transform of f2 yields F2, and the two-dimensional Fourier transform of f1 yields F1. As shown in FIGS. 13 and 14, the slice images f1 and f2 involve blood vessels 20a and 20b (e.g. aorta) only as the varying portions. Thus, if $g = (f2-f1)/2$ only blood vessel 20c appears at substantially the center of the MR image as a differential image. Accordingly, in the two-dimensional discrete inverse Fourier transformed image d for D, an image corresponding to blood vessel 20c in the g=(f2−f1)/2 image appears as images 20d and 20e in FIG. 16 at opposite ends in the encoding direction, in other words, at positions −π, and π spaced apart from the position of blood vessel 20c. Therefore, where the varying portion is not located at substantially the center of the MR image, broadening the field of view of the MR image would allow the artifacts not to overlap a portion of interest.

As described above, since the difference D between F and the average of F1 and F2 is F−(F1+F2)/2, when the excitation of the MR phenomenon and the collection of the MR signal are carried out in synchronism with the heartbeats and at an interval of aT, bT, aT, bT, ... the collected data F (refer to FIG. 8) is represented by $$F = D + \{(F1+F2)/2\} \quad (6)$$

Thus, the image f obtained by the two-dimensional discrete inverse Fourier transform of F is given by $$f = d + \{(f1+f2)/2\} \quad (7)$$

Figure 17:
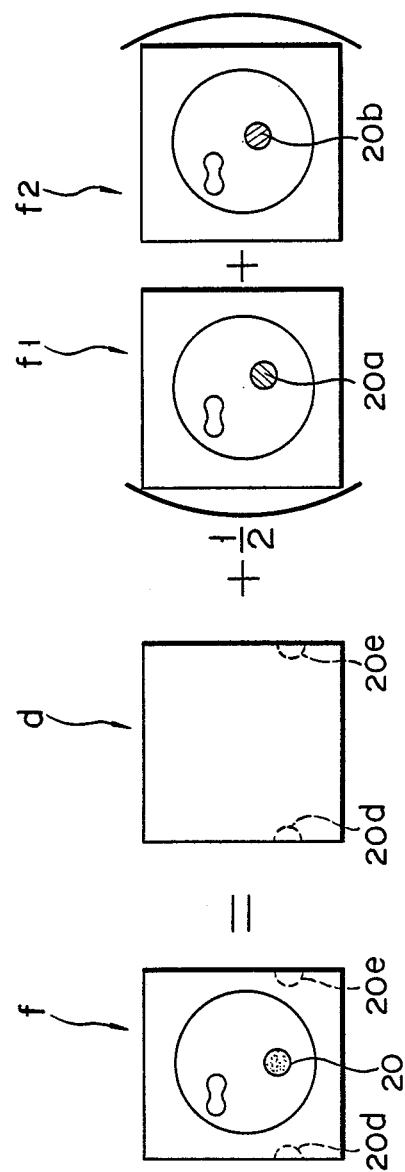

That is, the image f is given, as shown in FIG. 17, by the summation of the average of the two images f1 and f2 each involving no artifact and the image d having artifacts at opposite ends thereof and a gradation value of zero except for the artifacts. This image f is displayed and/or recorded as the MR image of the selected slice of the subject. It is seen that in the image f artifacts 20d and 20e appear at the opposite ends only, and no artifacts appear at the center. Thus, the image f is easy to watch as compared with the image in which many artifacts appear from the center to opposite ends thereof as shown in FIG. 6. Further, the image f allows easy and accurate diagnosis based on the MR image.

Reference is now made to FIG. 18 to describe an arrangement of MRI system embodying this invention based on the principle as described previously.

The MRI system of FIG. 18 comprises a static magnetic field generator 1, an RF pulse transmitter 2, a gradient magnetic field generator 3, a signal acquisition section 4, an image forming section 5, a system controller 7, and a heart beat detector 8. Heart beat detector 8 includes an electrocardiograph (ECG) 9 and an R wave detector 10.

Static field generator 1 applies a static magnetic field Ho to at least a region of subject P including a selected portion or slice to obtain an MR image for diagnosis. RF pulse transmitter 2 applies to subject P an RF pulse of RF magnetic field to excite an MR phenomenon. Gradient field generator 3 generates gradient magnetic fields which are superimposed on static magnetic field Ho. The gradient magnetic fields generated by gradient field generator 3 involves, as described above, a slicing gradient field Gz for selecting and determining a slice of subject P, and also a phase encoding gradient field Gy and a readout gradient field Gx, both for adding two dimensional information to MR signals.

Signal acquisition section 4 receives and acquires an MR signal resulting from the MR phenomenon excited in the subject P. Image forming section 5 receives the MR signal acquired by signal acquisition section 4 to reconstruct an MR image of the selected slice of subject P by predetermined processes including the two dimensional Fourier transform and the two dimensional discrete inverse Fourier transform as described above. Display section 6 visually displays the MR image formed by image forming section.

The heart beat information detected by heart beat detector 8 is applied to system controller 7. Electrocardiograph 9 in heart beat detector 8 detects heart electromotive force of subject P to provide an ECG signal. R wave detector 10 in heart beat detector 8 detects an R wave generated by excitation of ventricles from ECG waveform provided from ECG 9, thereby producing an R wave detect signal, which is in turn applied to system controller 7 as heart beat information.

Figure 1:
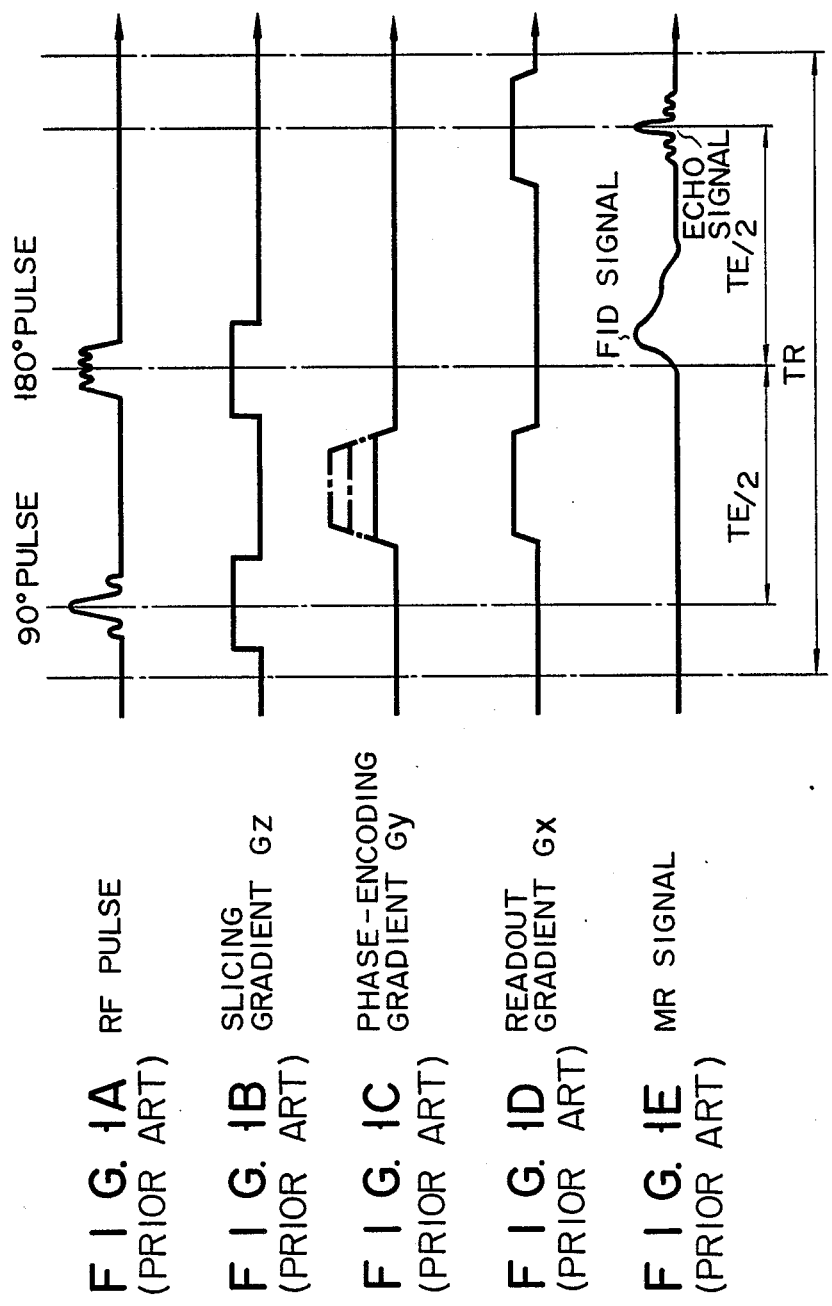
FIGS. 1A through 1E illustrate timing charts used for explaining a pulse sequence used in a conventional phase encoding method.

System controller 7 is responsive to the heart beat information to control the operations of static field generator 1, RF pulse transmitter 2, gradient field generator 3, and signal acquisition section 4. The pulse sequence shown FIG. 1 is executed by the control operation of system controller 7. System controller 7 repeats the pulse sequence on the basis of the heart beat information provided from heart beat detector 8 so that the excitation of MR phenomenon and the acquisition of MR signal are repeatedly carried out in synchronism with the heart beats of the subject P. In this case, supposing that the heart beat period is T, and a and b are coefficients to satisfy the relation a+b=1 (1>a>0, 1>b>0), system controller 7 operates to excite the MR phenomenon and acquire the MR signal at an interval of aT and bT.

The ECG signal of subject F is detected by ECG 9 in heart beat detector 8, and the R wave in the ECG waveform is detected from the ECG signal in R wave detector 10. System controller 7 finds the heart beat period T from the R wave detect signal, and then performs control operations such that the excitation of the MR phenomenon in the selected slice and the acquisition of the MR signal are executed at an interval of aT, bT, aT, bT, ... described above. In this way, the MR signal of the selected slice is acquired in signal acquisition section 4, and in turn applied to image forming section 5 to form the MR image of the selected slice. It is noted here that the MR signal is fed into image forming section 5 under the above described control of system controller 7. Since the MR signal loaded to image forming section 5 is data F expressed by equation (6), the image f obtained by two-dimensional discrete inverse Fourier transforming the data F in image forming section 5 becomes the summation of the average image of images f1 and f2 having the blood vessel located at the center and the image d having only the image artifacts of the blood vessel located at opposite ends of the image, as shown in FIG. 17. This image f is then visually displayed for diagnosis.

With this displayed image f the artifacts due to variation in blood flow rate locate at the opposite ends of the image, and do not appear at the center of the image, so that adverse effects due to the artifacts on the observation of the MR image and the following diagnosis can be almost avoided.

Moreover, in this case, the excitation of the MR phenomenon and the acquisition of the MR signal are executed two times during the heartbeat period T. Thus, the MR signal can be acquired in a time half that required in case where the excitation of the MR phenomenon and acquisition of the MR signal are executed once during the heartbeat period T in synchronism with the heartbeats.

This invention is not limited to the above described embodiment, and can be modified in various ways without departing from the scope of this invention.

For example, heartbeat detector 8 may be equipped with a phonocardiograph instead of electrocardiograph 9. Further, a selected slice may involve portions which vary in accordance with respiration other than portions such as blood vessels and heart which vary with heartbeats. With the portions which vary owing to respiration, by detecting the respiration and acquiring such MR signal as described above in synchronism with a respiration detect signal, the same MR image as above will be obtained.

The principle of this invention may be applied to not only portions which continuously vary, but also varying portions in which substantially at least two conditions appear alternately. In either case, the same advantage as above will be obtained. Further, this invention is effective in any case where the varying portions change in quality corresponding to the gradation in image, in size, or in shape.

What is claimed is:

1. A magnetic resonance imaging system comprising:
   static magnetic field forming means for forming a static magnetic field in a region including a selected slice of a subject having a varying portion which periodically varies in synchrony with heartbeats of said subject, and in which substantially at least two conditions of the varying portion of the subject alternately appear;
   gradient magnetic field applying means for applying gradient magnetic fields to said subject placed in the static magnetic field;
   high frequency magnetic field applying means for applying a high frequency magnetic field to at least said region including said selected slice of said subject for causing a magnetic resonance phenomenon in said region;
   signal acquiring means for detecting and acquiring a magnetic resonance signal produced in said selected slice of said subject by said magnetic resonance phenomenon;
   system control means for controlling said static magnetic field forming means, said gradient magnetic field applying means, said high frequency magnetic field applying means, and said signal acquiring means such that predetermined gradient and high frequency magnetic fields are repeatedly applied to said region including said selected slice of said subject in a predetermined sequence according to a phase encoding method to excite said magnetic resonance phenomenon in said selected slice, and the magnetic resonance signal due to the magnetic resonance phenomenon is acquired by said signal acquiring means;
   image forming means responsive to the magnetic resonance signal acquired by said signal acquiring means to obtain magnetic resonance image information of said selected slice of said subject; and
   heartbeat information detecting means for monitoring the heartbeats of said subject, and detecting timings of appearance of said at least two conditions, wherein
   said system control means is responsive to said heartbeat information detecting means to control the repetition of said predetermined sequence, and causing said signal acquiring means to alternately acquire magnetic resonance signals at the time of said at least two conditions.

2. A magnetic resonance imaging system according to claim 1, wherein
   said varying portion is a portion which varies in qualities of a predetermined tissue.

3. A magnetic resonance imaging system according to claim 1, wherein
   said varying portion is a portion whose condition continuously varies at a substantially regular period.

4. A magnetic resonance imaging system according to claim 3, wherein
   said heartbeat information detecting means detects a specified phase of the variation of said varying portion, and obtains the timings of said at least two conditions such that the timings define time intervals aT and bT, where T is a fundamental period of the heartbeats, and a and b are coefficients to satisfy $a+b=1 (1>a>0, 1>b>0)$.

5. A magnetic resonance imaging system according to claim 3, wherein
   said heartbeat information detecting means includes means for detecting an electrocardiographic information and detecting an R wave from the electrocardiographic information.

* * * * *